US00PP09542P

United States Patent [19]

Zaiger et al.

[11] Patent Number: Plant 9,542

[45] Date of Patent: May 7, 1996

[54] NECTARINE TREE 'ARCTIC SWEET'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 409,062

[22] Filed: Mar. 23, 1995

[51] Int. Cl.[6] ..... A01H 5/00

[52] U.S. Cl. ..... Plt./40.1

[58] Field of Search ..... Plt./40.1

*Primary Examiner*—James R. Feyrer

[57] ABSTRACT

A new and distinct variety of nectarine tree with the following unique combination of desirable features:

1. Heavy and regular production.
2. Vigorous, upright growth.
3. Mild, sweet subacid fruit with excellent flavor and eating quality.
4. Fruit with firm flesh, good storage and shipping quality.
5. Fruit with a high degree of attractive red skin color.

1 Drawing Sheet

ORIGIN OF THE VARIETY

The present new variety of nectarine tree was originated by us in our experimental orchard located near Modesto, Calif., as a second generation seeding from a cross between a selected seedling with the field identification number 97ED497 and June Glo Nectarine (U.S. Plant Pat. No. 5,228). The seedling selected with the identification number 97ED497, which is the female parent, originated from open pollinated White Lady Peach (U.S. Plant Pat. No. 5,821) seed grown by us. A large group of these second generation seedlings were planted and maintained under careful observation by us, during which time we recognized the desirable fruit characteristics described above and selected the present variety for asexual reproduction and commercialization.

ASEXUAL REPRODUCTION OF THE VARIETY

The new and distinct variety of nectarine tree was asexually reproduced by budding as performed by us, in our experimental orchard located near Modesto, Calif., which shows that all characteristics are established and transmitted through succeeding propagations and run true to the original tree in all respects.

SUMMARY OF THE VARIETY

The herein described variety of nectarine tree is large, vigorous, upright in growth and is a regular and productive bearer of large, firm, white flesh, clingstone fruit with excellent flavor and eating quality. The fruit is further characterized by having good storage and shipping quality, holding firm on the tree 6 to 7 days after maturity (shipping ripe) and in comparison to June Glo Nectarine (U.S. Plant Pat. No. 5,228) has white flesh instead of yellow flesh and is approximately 6 days later in maturity.

DESCRIPTION OF THE PHOTOGRAPHS

The accompanying color photograph shows reproductions of typical specimens of the foliage and fruit of the present new variety of nectarine tree. The illustration shows the upper and lower surface of the leaves and the exterior and sectional view of the fruit divided in the suture plane to show flesh coloration, pit cavity and a stone remaining in place. The photographs were taken shortly after the fruit was picked at maturity (firm ripe) and the colors are as nearly true as is reasonably possible in a color representation of this type.

DESCRIPTION OF THE VARIETY

The following is a detailed botanical description of the new and distinct variety of nectarine tree, its flowers, foliage and fruit, based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Shape.*—Usually pruned to vase shape.
- *Productivity.*—Productive.
- *Bearing.*—Regular.

Trunk:
- *Size.*—Large.
- *Texture.*—Medium shaggy.
- *Color.*—Brown to dark brown (6-E-5) to (6-F-5).

Branches:
- *Size.*—Medium.
- *Texture.*—Smooth to medium rough.
- *Lenticels.*—Numerous. Large size.
- *Color.*—Light brown to brown — varies with maturity.

Leaves:
- *Size.*—Large. Average length — 6½". Average width — 1½".
- *Form.*—Lanceolate — pointed.
- *Texture.*—Smooth.
- *Thickness.*—Medium.
- *Margin.*—Crenate.
- *Petiole.*—Medium length. Medium thickness.
- *Glands.*—Number varies from 2 to 6. Average number 3. Reniform. Medium size. Located on base of leaf blade and upper portion of petiole.
- *Color.*—Upper surface green to deep green (28-F-6) to (28-F-8). Lower surface light green to green (28-E-4) to (28-E-6).

Flower buds:
- *Size.*—Medium to large.
- *Length.*—Medium.
- *Form.*—Plump — free.

Flowers:
- *Size.*—Large — showy.
- *Blooming period.*— Mar. 1, 1993 to Mar. 6, 1993 Varies slightly with climatic conditions.
- *Pollen.*—Present — self fertile.
- *Color.*—Pink.

Fruit:

*Maturity then described.*—Firm ripe.

*Date of first picking.*—Jun. 12, 1993.

*Date of last picking.*—Jun. 17, 1993.

*Size.*—Large. Average diameter axially — 2⅞". Average transversely in suture plane — 2¾".

*Form.*—Nearly Globose.

*Suture.*—Shallow — extends from base to apex.

*Ventral surface.*—Very shallow — nearly round.

*Cavity.*—Rounded to slightly elongated in suture plane. Average depth ½". Average breadth ¾".

*Base.*—Retuse.

*Apex.*—Usually rounded, varies from round to slight pistil point.

Flesh:

*Ripens.*—Evenly.

*Texture.*—Firm.

*Amygdalin.*—Undetected.

*Juice.*—Moderate.

*Aroma.*—Moderate.

*Fibers.*—Small — tender.

*Flavor.*—Excellent.

*Eating quality.*—Excellent.

*Color.*—White to pinkish white (6-A-1) to (6-A-2).

*Pit cavity.*—White to yellowish white (4-A-1) to (4-A-2).

Skin:

*Thickness.*—Medium.

*Texture.*—Medium — tenacious to flesh.

*Tendency to crack.*—None.

*Down.*—Wanting.

*Color.*—Ground color — white to pinkish white (6-A-1) to (6-A-3). Overspread with lobster red to red (9-B-8) to (9-D-8).

Stone:

*Type.*—Clingstone.

*Size.*—Large. Average length 1½". Average breadth 1". Average thickness ⅝".

*Form.*—Oval to ovoid.

*Base.*—Usually straight — varies from rounded to straight.

*Apex.*—Usually cuspidate — varies from cuspidate to rounded.

*Side.*—Mostly unequal — varies from unequal to equal.

*Surface.*—Irregularly furrowed toward apex, pitted toward base. Pits elongated to round.

*Ridges.*—Round.

*Tendency to split.*—Very slight.

*Color.*—Cinnamon brown to leather brown (6-d-6) to (6-E-6).

Use: Dessert.

*Market.*—Local and long distance.

Keeping quality: Good.

Shipping quality: Good.

The nectarine tree, its flowers, foliage and fruit herein described may vary in slight detail due to climate, soil type and cultural practices under which the variety may be grown. The present description is that of the variety grown under the ecological condition prevailing near Modesto, Calif.

We claim:

1. A new and distinct variety of nectarine tree, substantially as illustrated and described, which is of large size, vigorous upright growth and which is a productive and regular bearer of large, white flesh, clingstone fruit with excellent flavor and eating quality; the fruit is further characterized by having firm flesh with good storage and shipping quality, having an attractive red skin color and in comparison to its pollen parent June Glo Nectarine (U.S. Plant Pat. No. 5,228), has white flesh instead of yellow and is approximately 6 days later in maturity.

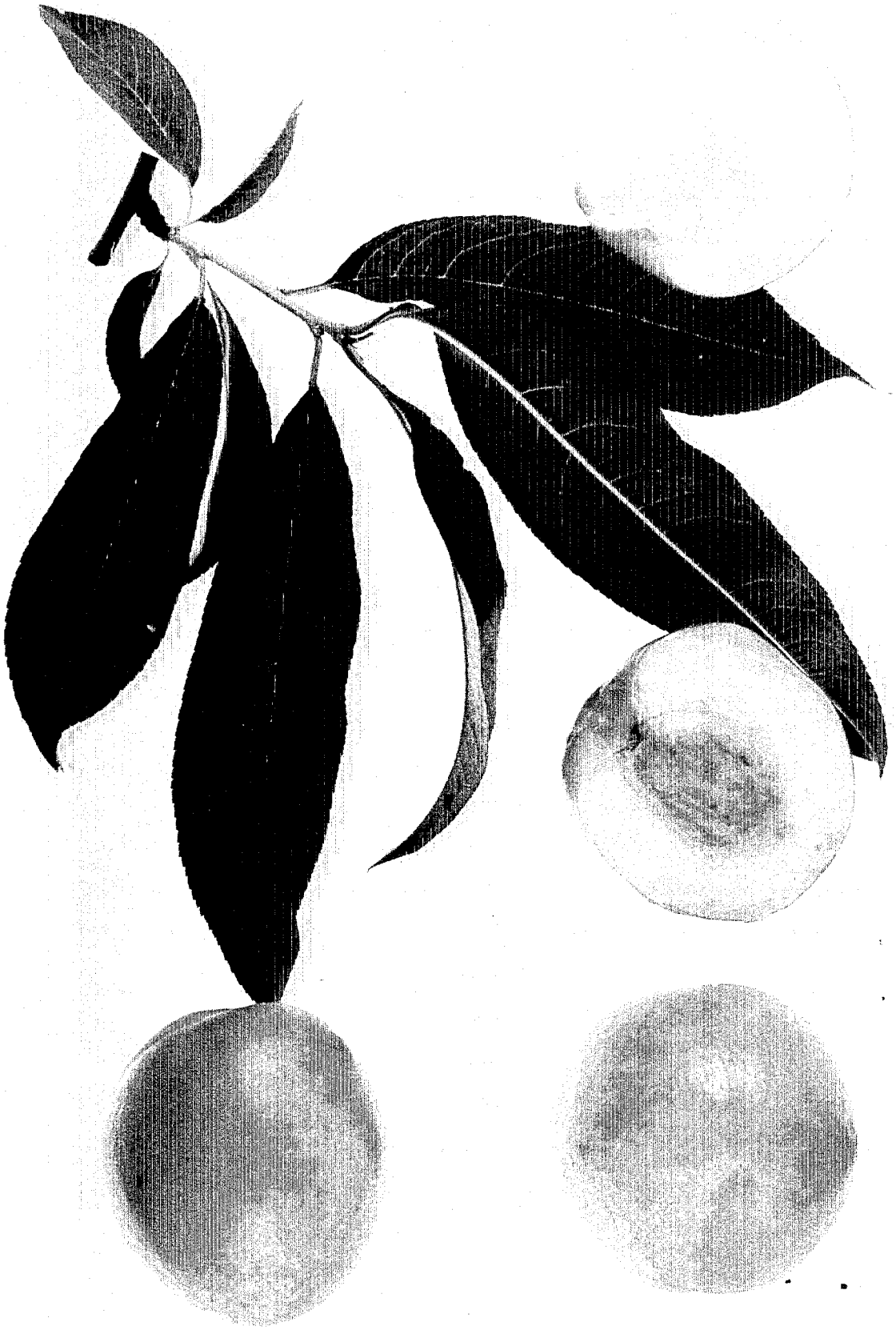

* * * * *